United States Patent [19]

Hatanaka et al.

[11] Patent Number: 4,797,255

[45] Date of Patent: Jan. 10, 1989

[54] STERILIZATION METHOD AND APPARATUS THEREFOR

[75] Inventors: Koichi Hatanaka, Sayama; Yoshito Shibauchi, Kawagoe, both of Japan

[73] Assignee: Snow Brand Milk Products Co., Ltd., Hokkaido, Japan

[21] Appl. No.: 26,384

[22] Filed: Mar. 16, 1987

[30] Foreign Application Priority Data

Mar. 24, 1986 [JP] Japan ............................ 61-65346
Jul. 24, 1986 [JP] Japan ............................ 61-174235

[51] Int. Cl.$^4$ ............................ A61L 2/18; A61L 2/20
[52] U.S. Cl. ............................ 422/28; 422/292; 422/304
[58] Field of Search ............................ 422/24, 28, 33, 304, 422/292

[56] References Cited

U.S. PATENT DOCUMENTS

| | | | |
|---|---|---|---|
| 4,289,728 | 9/1981 | Peel et al. | 422/24 |
| 4,366,125 | 12/1982 | Kodera et al. | 422/24 X |
| 4,424,189 | 1/1984 | Hick | 422/28 X |
| 4,512,951 | 4/1985 | Koubek | 422/33 |
| 4,642,165 | 2/1987 | Bier | 422/28 X |
| 4,643,876 | 2/1987 | Jacobs et al. | 422/28 X |
| 4,680,163 | 7/1987 | Blidschun et al. | 422/28 |

FOREIGN PATENT DOCUMENTS

3440714 6/1985 Fed. Rep. of Germany ........ 422/28
220067 11/1984 Japan .

Primary Examiner—Benoit Castel
Assistant Examiner—Jill Johnston
Attorney, Agent, or Firm—Griffin, Branigan & Butler

[57] ABSTRACT

A hydrogen peroxide gas maintained at a temperature which is higher than its condensing temperature at the least is admitted to a surface of an object to be sterilized, the hydrogen peroxide gas is condensed on the surface of the object maintained at a temperature below the condensing temperature to sterilize the object, and thereafter the hydrogen peroxide is removed by hot air.

4 Claims, 4 Drawing Sheets

STERILIZATION METHOD AND APPARATUS THEREFOR

BACKGROUND OF THE INVENTION

This invention relates to a sterilization method and an apparatus therefor.

In the past, it has already been practiced to sterilize packing articles such as vessels by using hydrogen peroxide. Specifically, a packing article is, in one method, immersed in hydrogen peroxide and in another method atomized hydrogen peroxide is sprayed to a packing article.

Where the packing article sterilized according to the conventional methods as above is a sheet or takes a sheet-like form, droplets of hydrogen peroxide deposited on the packing article can be removed readily by, for example, blowing hot air to the packing article. However, a cubic packing article having a deep depth or a complicated form faces problems in being removed of the sterilizer. More particularly, hydrogen peroxide can not be removed from part of a cubic packing article sterilized according to the immersing method, and in the case of a cubic packing article sterilized according to the spraying method, removal of hydrogen peroxide from the exterior surface of the packing article is relatively easy but hydrogen peroxide sprayed and deposited on the side wall interior surface, for example, is liable to keep staying in the packing article and it takes a long time to remove such staying hydrogen peroxide.

To cope with these problems, the inventors of the present invention have already proposed a so-called gasification and atomization method as disclosed in Japanese Patent Application Laid-open No. 60-220067. According to this proposal, hydrogen peroxide is atomized into fine droplets, and a hydrogen peroxide film is formed of a small amount of the hydrogen peroxide fine droplets substantially uniformly over the entire surface of even a packing article of a complicated form. The hydrogen peroxide film can be removed efficiently. Thus, this proposal solves the problems encountered in both the conventional methods described previously.

The gasification and atomization method is advantageous as described above but it is still disadvantageous in that because of atomization of the hydrogen peroxide by way of an atomizer nozzle, a pressurizing unit for pressurizing the hydrogen peroxide and an atomization chamber are required, making the overall apparatus complicated, that the atomizer nozzle becomes clogged and the atomization suffers from hunting, resulting in troubles during running of the apparatus and that the consumption of the hydrogen peroxide increases.

SUMMARY OF THE INVENTION

It is accordingly an object of this invention to provide method and apparatus for sterilization which can sterilize very efficiently an object to be sterilized such as a packing article independently of its form with minimized consumption of hydrogen peroxide and which can remove, after completion of sterilization, the hydrogen peroxide from the entire surface of the sterilized object within a minimized time without leaving behind any residual of the hydrogen peroxide.

According to the present invention, the above object can be accomplished by a method for sterilization wherein a hydrogen peroxide gas maintained at a temperature which is higher than its condensing temperature at the least is admitted to a surface of an object to be sterilized, the hydrogen peroxide gas is condensed on the surface of the object maintained at a temperature below the condensing temperature to sterilize the object, and thereafter the hydrogen peroxide is removed by hot air.

Another object of this invention is to provide sterilization method and apparatus which can further reduce the amount of hydrogen peroxide to be condensed on the surface of the object to be sterilized to ensure uniform condensation and further reduce the time for removal of the hydrogen peroxide.

According to this invention, the second object can be accomplished by a method for sterilization wherein a hydrogen peroxide liquid is dropped in the form of liquid droplets each having the size, preferably being of 1 to 3 mm diameter, which permits the hydrogen peroxide liquid to be gasified instantaneously and to be dropped, toward an evaporation surface of a heater heated to a temperature above 130° C., preferably 140° C. to 180° C., at which the decomposition of the hydrogen peroxide during gasification is minimized and the dropped hydrogen peroxide liquid is gasified at the evaporation surface, a hydrogen peroxide gas thus generated is admitted by transport air heated to a temperature which is substantially equal to or higher than the temperature of the evaporation surface to a surface of an object to be sterilized through a guide pipe heated to a temperature which is substantially equal to or higher than the temperature of the evaporation surface, the hydrogen peroxide gas is condensed at the surface of the object maintained at a temperature which is lower than the condensing temperature of the hydrogen peroxide gas so as to sterilize the object, and thereafter the hydrogen peroxide is removed by hot air.

In practicing the sterilization method as above, a sterilization apparatus according to the invention is used which comprises feeder means for feeding a constant amount of hydrogen peroxide liquid, means for gasifying the hydrogen peroxide liquid fed from the feeder means by heating, transport air supply means for supplying air which transports a hydrogen peroxide gas generated by the gasifying means, and guide means for admitting the hydrogen peroxide gas to a surface of an object to be sterilized while maintaining the hydrogen peroxide gas at its evaporation temperature.

Generally, the sterilization effect of the hydrogen peroxide depends on concentration of the hydrogen peroxide and temperatures, and it can be activated by raising the temperature. Accordingly in the prior art method for sterilization with hydrogen peroxide, especially, in an invention disclosed in the aforementioned Japanese Patent Application Laid-open No. 60-220067, the hydrogen peroxide is atomized by means of an atomization nozzle and heated to a temperature in a range within which the sterilization effect is highly activated.

However, from the standpoint of safety, the temperature of the hydrogen peroxide can not be raised to so high a value even if this value falls within the sterilization effect activating range.

On the contrary, according to the invention, a hydrogen peroxide gas maintained at a higher temperature than its condensing temperature is admitted to a surface of an object to be sterilized and condensed at the object surface maintained at a lower temperature than the condensing temperature so as to sterilize the object, whereby the hydrogen peroxide gas having a droplet diameter which is smaller than that of the atomized hydrogen peroxide can be deposited on the surface of the object to be sterilized. Consequently, the hydrogen peroxide gas can be deposited at high concentration to promote the sterilization effect and hence an amount of the hydrogen peroxide duly required for the packing article surface can be deposited with minimized consumption of the hydrogen peroxide within a decreased drying time.

This will be described in greater with reference to FIG. 1.

Figure 1:
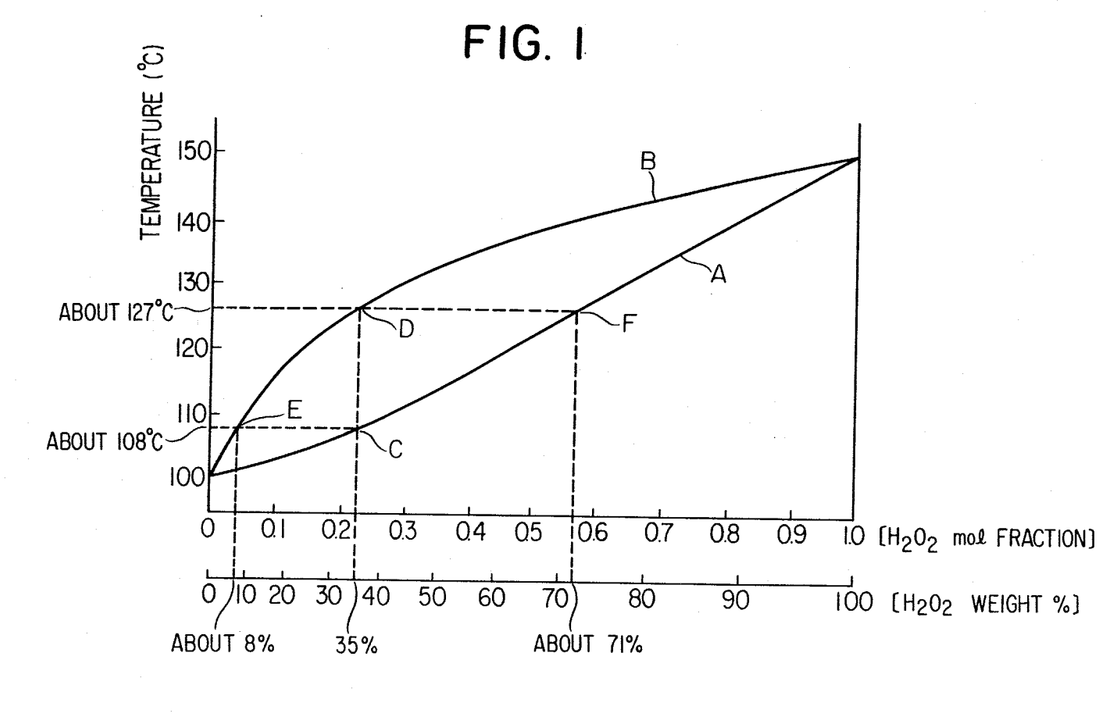
FIG. 1 is a graph showing an evaporation characteristic of hydrogen peroxide and a corresponding hydrogen peroxide gas composition characteristic.

FIG. 1 illustrates an evaporation characteristic of hydrogen peroxide at 760 mmHg and a gas composition of a hydrogen peroxide gas generated during evaporation, wherein ordinate represents equilibrium temperatures of liquid phase and gas phase and abscissa represents concentration of hydrogen peroxide solution in weight % and mol fraction. For convenience of explanation, $H_2O_2$ is taken for the hydrogen peroxide in describing FIG. 1.

Referring to FIG. 1, the boiling point of $H_2O_2+H_2O$ solution changes with concentration as indicated by a curve A and the gas composition at the boiling point changes with concentration as indicated by a curve B.

Generally, where a solution is of two kinds of liquid having different boiling points (condensing temperatures) and especially where a $H_2O_2$ solution which is a mixture liquid of $H_2O$ and $H_2O_2$ is concerned in which the former constituent has a boiling point which is lower than that of the latter, $H_2O$ begins to evaporate earlier than $H_2O_2$ and $H_2O_2$ begins to condense earlier than $H_2O$.

When taking a 35% $H_2O_2$ solution at a boiling point C, i.e., at 108° C., a corresponding gas composition is found at a point E and $H_2O_2$ gas concentration is 8%, as will be seen from FIG. 1.

Namely, the gas composition in equilibrium with that liquid phase at 108° C. is of 8% $H_2O_2$ concentration.

A $H_2O_2$ solution of 71% concentration begins to evaporate at a boiling point F, i.e., at 127° C. A corresponding gas composition in equilibrium with that liquid phase is of 35% $H_2O_2$ concentration.

Accordingly, on the assumption that the 35% $H_2O_2$ solution is not decomposed and this solution is all gasified, the corresponding gas composition is of 35% $H_2O_2$ concentration and this gas composition of 35% $H_2O_2$ concentration, when cooled, comes into equilibrium with the $H_2O_2$ solution of 71% liquid phase concentration.

In other words, when the gas composition stemming from complete gasification of the hydrogen peroxide solution of 35% concentration is cooled and condensed, the condensation liquid becomes highly concentrated, amounting to 71% concentration, at the commencement of the condensation. This highly concentrated condensation liquid can be used for sterilization, attaining a high sterilization effect because the concentration of the hydrogen peroxide and the temperature govern the sterilization effect.

In this manner, according to this invention, the hydrogen peroxide gas is condensed at high concentration at the initial phase and used for sterilization. The highly concentrated hydrogen peroxide condensation liquid is deposited, in the form of a thin film, on the packing article surface, thereby attaining a high sterilization effect.

It should be appreciated from the foregoing description that the hydrogen peroxide experiencing the gasification to condensation process can be condensed at the surface of the object to be sterilized at higher concentration than that of the hydrogen peroxide solution involved.

In addition, the hydrogen peroxide to be condensed is admitted in the gaseous form to the surface of the object to be sterilized and readily distributed uniformly, in the form of a thin film, on the object surface even if the surface configuration is complicated. The uniform thin film can be removed very easily by drying.

Where irradiation of ultraviolet rays is used for sterilization in combination with the application of the hydrogen peroxide, the thickness of the hydrogen peroxide film need not be so large and consequently, the transmittivity of the ultraviolet rays can be increased to attain a high sterilization effect with a thin hydrogen peroxide film used.

Since the evaporation unit according to the invention does not use any atomizer nozzle, it is not necessary to provide a unit for pressurizing the hydrogen peroxide and an atomization chamber to thereby simplify the overall apparatus, and such troubles as nozzle clogging and atomization hunting will not take place during operation.

In the invention the liquid droplets dropping toward an evaporation surface of a heat generator have each the size, preferably being of about 1 to 3 mm diameter, which permits the hydrogen peroxide liquid to be gasified instantaneously and to be dropped. Liquid droplets of larger size adversely lower the temperature of the evaporation surface to decrease evaporation efficiency and to increase decomposition percentage. Liquid droplets of smaller size are difficult to form by using a dropping nozzle (when the diameter of the nozzle is made small, the liquid is prevented from dropping because of surface tension and sticks to the tip of the nozzle), or they tend to be atomized in an excessive amount and to cause nozzle clogging when formed by means of two fluid nozzles. If the liquid is atomized using ultrasonic waves, the liquid droplets become so small as to suspend and the suspending droplets can not drop to the evaporation surface.

To reduce the decomposition of the hydrogen peroxide during gasification and minimize the time required for the hydrogen peroxide to evaporate, the evaporation surface is heated to a temperature above 130° C., preferably 140° C. to 180° C. The evaporation surface at a temperature outside the range of from 140° C. to 180° C., especially below 140° C., increases the decomposition percentage of the hydrogen peroxide and is therefore unpractical.

Thermal distribution on the evaporation surface is made uniform by transferring heat generated by the heat generator to the evaporation surface through a heat transfer member of high thermal conductivity or a heat transfer mechanism such as a heat pipe.

In order to prevent the dropped liquid droplets from moving on the evaporation surface so that they collide with each other to grow into larger droplets, the evaporation surface is preferably formed with grooves, provided with partition walls or mounted with a mesh. To promote gasification, transport air is preferably blown to the evaporation surface horizontally thereof because gasification efficiency is higher when the transport air is blown horizontally of the evaporation surface than when blown vertically of the evaporation surface.

Since heat necessary for the gasification is principally supplied from the evaporation surface, the transport air rapidly carries away the generated gas to decrease the thickness of a boundary layer between the liquid and gas phases, contributing to further promotion of the gasification.

Preferably, the temperature of the transport air is made substantially equal to or higher than the temperature of the heat generator to ensure that the temperature of the generated gas can be prevented from lowering.

The amount of transport air is so controlled as to be minimized while ensuring that the temperature of a mixture gas of the hydrogen peroxide gas and transport air can fall within a range of from about 140° C. to about 200° C. An excessive amount of the transport air decreases the dew point and the efficiency of condensation of the hydrogen peroxide gas on the surface of the object to be sterilized is decreased. This requires that the amount of the transport air be small but too small an amount of the transport air looses ability to transport.

A guide pipe through which the mixture gas is admitted to the surface of the object to be sterilized is heated to a temperature which is equal to or higher than that of the evaporation surface, preferably, 140° C. to 180° C.

The amount of the hydrogen peroxide gas condensed on the surface of the object to be sterilized is very small and the gas condensation is uniformly distributed. Accordingly, the condensed gas can be readily removed by drying.

To obtain a high combinational effect by using the ultraviolet rays in combination with the application of the hydrogen peroxide, the ultraviolet rays must be irradiated simultaneously with the condensation, preferably, in the absence of hot air or cold air.

DESCRIPTION OF THE PREFERRED EMBODIMENTS

Figure 2:
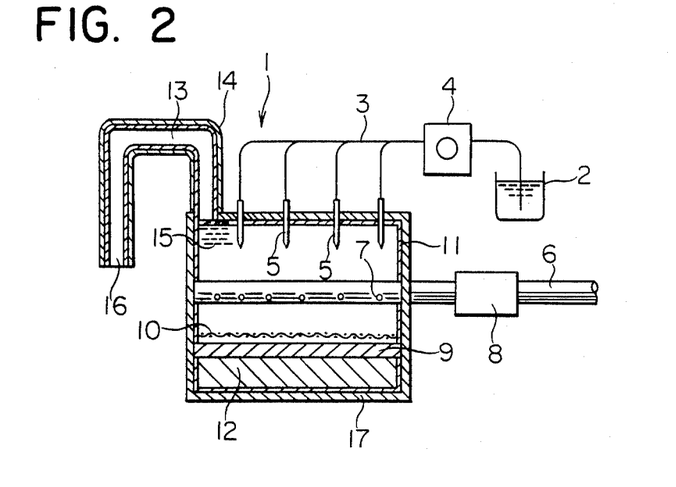
FIGS. 2 and 3 are longitudinal sectional views illustrating hydrogen peroxide gas generators according to different embodiments of the invention.

FIG. 2 illustrates an embodiment of a hydrogen peroxide gas generator, generally designated at reference numeral 1, used in a sterilization apparatus of the invention.

Referring to FIG. 2, a tank 2 for storage of a hydrogen peroxide solution is provided in which one open end of a pipe conduit 3 is located. A constant amount supply pump 4 is inserted in the pipe conduit 3. The other end of the pipe conduit 3 branches to a plurality of branch pipes each of which is mounted, at its end, with a droplet supply nozzle 5.

The nozzles 5 are supported in the top wall of a gasification chamber 11 and their nozzle openings are in communication with the interior of the chamber 11. The chamber 11 is surrounded by a heat insulating material 17. An air supply pipe 6 is inserted into the chamber 11 to lie beneath the droplet supply nozzles 5, germ-free air for pneumatic transportation being fed through the air supply pipe 6. The air supply pipe 6 has a portion, internal of the chamber 11, which is formed with a plurality of air supply holes 7 and an external extension in which a heater 8 is inserted.

Within the chamber 11, a heat transfer block 9 is supported beneath the air supply pipe 6. A stainless steel mesh 10 is provided above the heat transfer block 9 and a heat source block 12 is provided under the block 9.

Mounted at one end of the top of the chamber 11 is an inverted U-shaped guide 13 which is surrounded by a heater 14. The guide 13 communicates with the interior of the chamber 11 through a filter 15.

Figure 3:
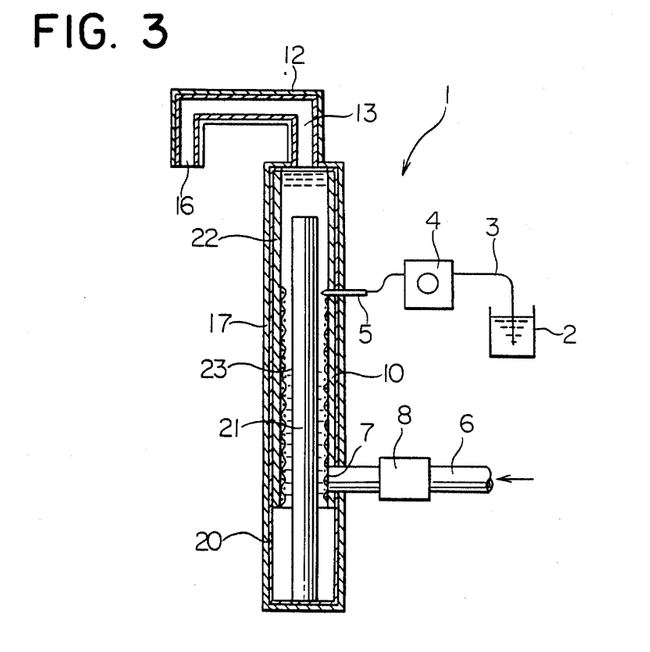

FIG. 3 illustrates another embodiment of the hydrogen peroxide gas generator. In FIG. 3, identical members to those of FIG. 2 are designated by identical reference numerals and the following description will be directed to different members.

In contrast to the gasification chamber 11 of FIG. 2 the gas generator of FIG. 3, also generally designated at reference numeral 1, has a vertical type gasification chamber 20. A droplet supply nozzles 5 extend laterally of the gasification chamber 20 and are supported in one side wall thereof. Within the chamber 20, a heat pipe 21 extends substantially along the center axis of the chamber 20 and a second heat pipe 22 mounted on the inner wall surface of the chamber 20 surrounds the heat pipe 21. The outer circumferential surface of the heat pipe 21 is provided with a plurality of fins 23 and the inner surface of the second heat pipe 22 is mounted with a stainless steel mesh 10.

In the embodiments of FIGS. 2 and 3 described previously, each of the heat source block 17 and heat pipes 21 and 22 comprises a temperature controllable member and any of an electric heater, a steam heater and a burner may exemplarily be used. The heat transfer block 9 is made of a material of high thermal conductivity such as copper or aluminum or alternatively, it may be of a heat pipe type.

The surface of the heat transfer block 9 and of the heat pipes 21 and 22 forms an evaporation surface and it must therefore be made of a corrosion-resisting material such as stainless steel. Liquid droplets tend to undergo a spheroidal phenomenon on the evaporation surface to turn to spheroidal liquid droplets. With the aim of preventing the spheroidal liquid droplets from colliding with each other to grow into larger droplets, the mesh 10 is provided and it prevents the spheroidal liquid droplets from moving freely. Preferably, this mesh may be of a multilayer structure.

The gas generator 1 operates to generate a hydrogen peroxide gas as will be described below.

Considering that the decomposition percentage of the hydrogen peroxide during gasification is affected by the temperature at the heat surface of the heat generator, the temperature at the heat surface has to be kept constant when the decomposition percentage is desired to be constant. Accordingly, in the foregoing embodiments, the amount of the hydrogen peroxide solution to be supplied to the gasification chamber 11 or 20 is kept constant by means of the pump 4 so that the heating temperature at the heat surface of the heat generator may be kept constant.

In supplying the liquid droplets to the gasification chamber 11 or 20 through the droplet supply nozzles 5 by using the pump 4 in this manner, the smaller the size of the supplied droplets, the easier the gasification becomes. However, the liquid need not be atomized and the size of the liquid droplets can be of the order, preferably being of 1 to 3 mm diameter, which does not prove a hindrance to the gasification. With the conventional and presently available one fluid nozzle or two fluid nozzles adapted for a small amount atomization, clogging tends to occur and with the spray nozzle, liquid must be pressurized for spraying. On the contrary, better results can be obtained by using the clogging-free, pressurizing-free droplet supply nozzles 5 which permit the use of the constant amount pump 4 of relatively small capacity and consequently by realizing the aforementioned size of the liquid droplets by means of the droplet supply nozzles 5.

The thus supplied hydrogen peroxide liquid droplets are heated for evaporation by the evaporation surface of the heat transfer block 9 or of the heat pipes 21 and 22. During the evaporation, the evaporation surface is heated by the heat source to a temperature, for example, above 130° C., preferably 140° to 180° C., at which the decomposition of the hydrogen peroxide can be minimized during the evaporation or gasification.

Figure 5:
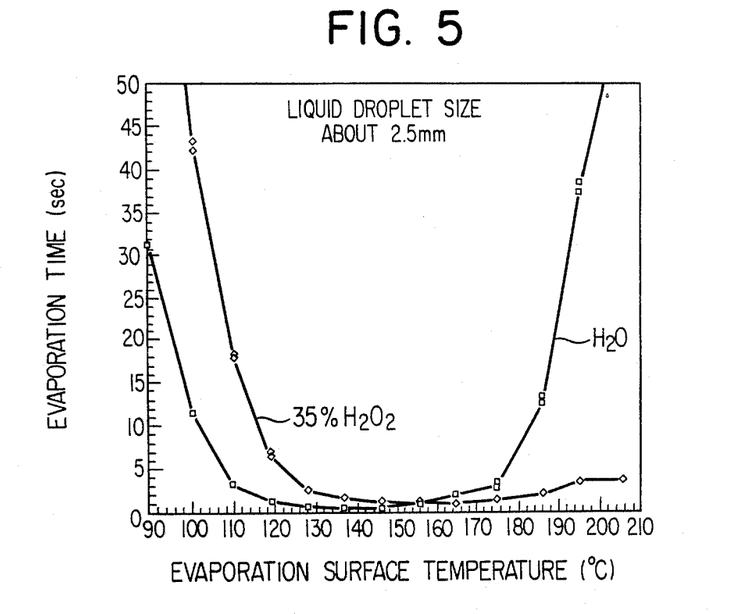
FIG. 5 is a graph showing the relation between evaporation surface temperature and evaporation time.

FIG. 5 graphically shows the relation between the evaporation time of a mixture solution of water and 35% concentration hydrogen peroxide and the evaporation surface temperature, indicating that the aforementioned temperature is suitable for instantaneous gasification.

The hydrogen peroxide of 35% concentration will decompose at a decomposition percentage of 17 to 18%.

While the hydrogen peroxide liquid droplets are supplied to the chamber 11 or 20 in the manner described previously, air is supplied to the interior of the chamber through air supply holes 7 in the air supply pipe 6. This air promotes the gasification of hydrogen peroxide on the evaporation surface of the heat transfer block 9 or of the heat pipe 21. In order that the thus gasified hydrogen peroxide can be admitted to the surface of the object to be sterilized through the guide pipe 13 while being maintained at a high temperature of about 140° C. to 180° C., the air is heated by the heater 8 to a high temperature of about 140° C. to 180° C. With the view of facilitating the gasification of hydrogen peroxide, the air is blown from the air supply holes 7 in parallel with gasification planes in the apparatus of FIG. 2.

When the hydrogen peroxide gas is admitted to the guide pipe 13, the gas will not grow to liquid droplets if the gasification is carried out rapidly in the chamber 11 or 20 but if the amount of the transport air increases or the spheroidal phenomeno takes place at the evaporation surface, then the gas will be coexistent with bubbles of liquid droplets. The filter 15 can prevent passage of such bubbles.

To prevent the hydrogen peroxide gas under pneumatic transport through the guide pipe 13 from being condensed, the guide pipe 13 is heated by the heater 14 to a temperature which is substantially equal to or higher than the temperature of the evaporation surface, for example, 140° C. to 180° C.

The hydrogen peroxide gas thus transported through the guide pipe 13 is discharged from an outlet 16 of the guide pipe 13 and directed to the surface of the object to be sterilized (not shown) so as to be deposited thereon. Experimentally, when a hydrogen peroxide gas of 35% concentration at 170° C. is deposited on the object to be sterilized having a surface temperature of 25° C., a hydrogen peroxide film of 55% condensation concentration can be formed. The film acts for sterilization and after completion of sterilization, it is dried for removal.

The hydrogen peroxide is in gasified state during deposition and is more reduced in size than the atomized hydrogen peroxide. This permits easy removal of the deposited hydrogen peroxide and especially, the film in the above experimental case can be completely removed within five seconds at a drying temperature of 80° C. For comparison, the atomization method takes ten seconds for removal at 120° C.

Figure 4:
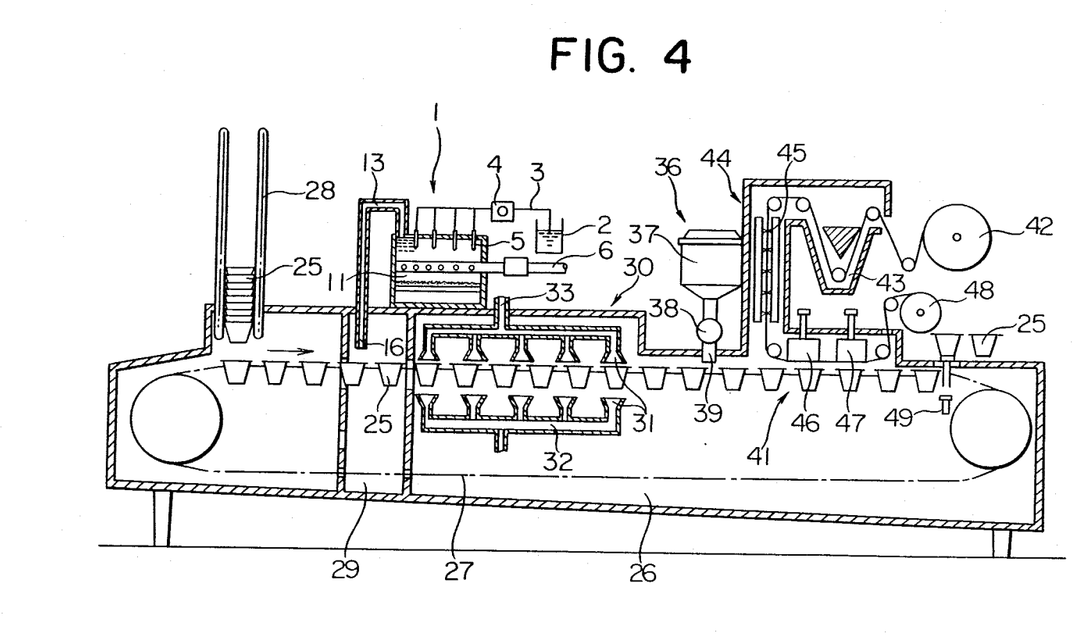
FIG. 4 is a longitudinal sectional view showing an example of a germ-free packing machine using the hydrogen peroxide gas generator.

Referring to FIG. 4 there is illustrated a germ-free packing machine equipped with the hydrogen peroxide gas generator 1 shown in FIG. 2.

Inside a germ-free chamber 26, a chain conveyor 27 is so arranged as to be movable in a direction of arrow, and vessels 25 are conveyed by means of the conveyor 27. At one end of the top of the chamber 26, a holder 28 stands uprightly and the vessels collectively held in the holder 28 are picked from below by a picker not shown and sequentially transferred to the conveyor 27.

The vessels 25 thus transferred to the conveyor 27 are conveyed to a sterilization chamber 29 at which the vessels 25 are sterilized in the manner described previously with the hydrogen peroxide gas jetting out of the outlet 16 of the guide 13 of the hydrogen peroxide gas generator 1.

The thus sterilized vessels 25 are then conveyed to a drying section 30. Inside the drying section 30, an air box 32 is supported which has a plurality of nozzles 31 arranged along the conveyance direction above and below the conveyor carrying the vessels 25. Germ-free heating air is supplied from an air supply pipe 33 to the air box 32 and it jets out of the nozzles 31 to the entire surface of each vessel 25. The drying section 30 also incorporates an ultraviolet-ray irradiator not shown which irradiates ultraviolet rays onto the entire surface of each vessel 25.

The vessels 25 thus removed of the hydrogen peroxide are conveyed to a charger section 36 at which the content such as completely sterilized foodstuffs is discharged from a storage tank 37 and charged into the vessel 25 through a nozzle 39 by the action of a valve 38.

Subsequently, the vessels 25 are conveyed to a cap sealing section 41. A roll cap material 42 is provided above the sealing section 41. The roll cap material 42 is paid out toward a sterilization tank 43 and the opposite side surfaces of the sterilized material are dried at a drying unit 44 by using germ-free air jetting out of a nozzle 45. The cap material 42 is then drawn out of the drying unit 44 into the cap sealing section 41 so as to overlie the vessels 25 in substantially parallel relationship with inlets of the vessels 25. Then the cap material 42 is sealed to the inlet of the vessel 25 by means of a sealing member 46 and thereafter stamped by means of a stamper 47 and finally reeled off by a reel 48.

The vessel 25 thus sealed with cap is then pushed up by a pusher 49 so as to be delivered out of the chamber 26.

In this charging and packing machine, the ultraviolet rays are used for sterilization in combination with the application of the hydrogen peroxide as described above, attaining a high combinational effect and therefore the amount of the hydrogen peroxide liquid used can be reduced to about 5% in weight. The combination of the hydrogen peroxide liquid droplets and ultraviolet rays has already been known as disclosed in Japanese Patent Publication No. 56-50058. However, this invention distinctively differs from the known technique in that while in the known technique the effect can be maximized by using a hydrogen peroxide liquid of 0.1 to 1% concentration, the sterilization effect is increased in proportion to the concentration in the present invention.

Figure 6:
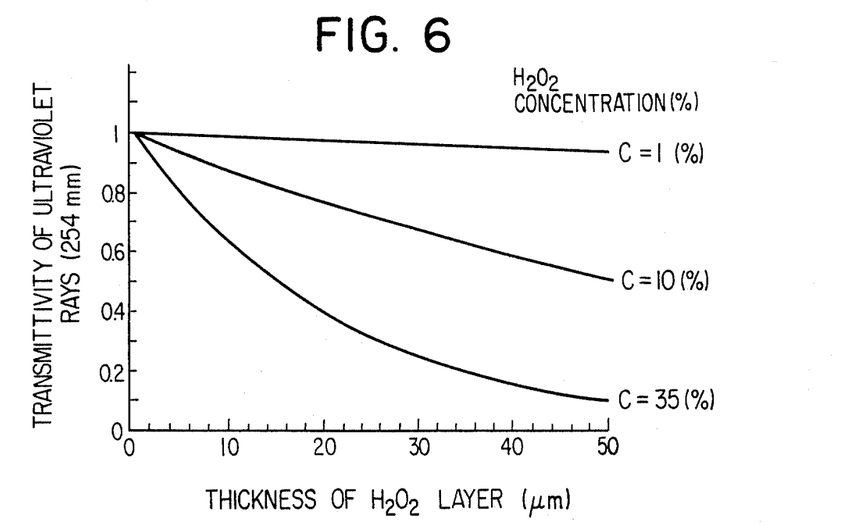
FIG. 6 is a graph showing the relation between the thickness of hydrogen peroxide film and the transmittivity of ultraviolet rays.

To explain the difference, the ultraviolet rays (typically, 254 mm -wavelength ultraviolet rays are used for sterilization) are very liable to be absorbed by the hydrogen peroxide and about 99% of the ultraviolet rays is absorbed by a thickness of about 100 micron meter of hydrogen peroxide of 35% concentration, failing to reach the surface of the object to be sterilized. However, the thickness of the condensation layer in accordance with the invention is considered to be very small, measuring about 1 micron meter and the ultraviolet rays are absorbed by this layer at an absorption factor of about 5%, thus efficiently reaching the surface of the object to be sterilized. This is indicated in FIG. 6 which shows that the transmittivity of ultraviolet rays increases as the thickness of the hydrogen peroxide film decreases.

As will be seen from the above, the method of this invention is highly effective and efficient for sterilization by having ability to effectively obtain the combinational effect attributable to the combination of the hydrogen peroxide and ultraviolet rays and to decompose and remove the condensed hydrogen peroxide very easily.

A sterilization apparatus in which a hydrogen peroxide aqueous solution is condensed to form a liquid layer on an object to be sterilized has been known as disclosed in Japanese Patent Publication No. 61-4543. However, in this known apparatus, sterilization is carried out under reduced pressure and in contrast to sterilization of the present invention based on continuous flow, the known apparatus, is of the batch type and its operation is too complicated to perform efficient sterilization.

More specifically, as will be seen from FIG. 1, the hydrogen peroxide liquid of 35% concentration must be heated to a temperature above 127° C. so as to be gasified completely and the gasified hydrogen peroxide must be cooled to a temperature below 127° C. so as to be condensed. At a temperature below 108° C., the 35% concentration can be recovered. If the gasified hydrogen peroxide is maintained at a temperature below 127° C., for example, at a temperature above 120° C., then a hydrogen peroxide condensation liquid of 63% concentration will be obtained. But it is impossible for the batch type apparatus to continuously remove other gases then the hydrogen peroxide in order to constantly obtain the hydrogen peroxide condensation liquid of 63% concentration while maintaining the 120° C. temperature.

Further, Japanese Patent Publication No. 61-9163 discloses a method for sterilizing an object by using a liquid sterilizer wherein the sterilizer is atomized into a mist which is admixed with a high temperature air flow, the temperature of the air and the ratio between sterilizer amount and air amount are controlled so that the sterilizer is vaporized and the dew point of the air mixed with the sterilizer becomes higher than a temperature of the surface to be sterilized, the air mixture is then admitted to the surface to be sterilized which cools the air mixture in order that the sterilizer is condensed in the form of a uniform layer on that surface so as to react for a predetermined time, and thereafter the sterilizer is again removed. In this known method, the quantity of heat necessary for gasifying the hydrogen peroxide is obtained from the heated air. But due to the fact that air has a small specific heat which is 0.24 Kcal/Kg.°C., a great amount of air or very high-temperature air is required for gasifying a great amount of hydrogen peroxide and there is involved a troublesome problem in either case. More specifically, the great amount of air dilutes the mixture gas to decrease the dew point thereof to make the mixture gas difficult to dew, thereby decreasing condensation efficiency. In addition, the flow rate increases as the amount of air increases, giving rise to problems that the size of the mixing chamber necessary for sufficient gasification is increased and that most of the mixture gas is discharged without maturing into condensation. The high-temperature air will possibly cause pyrolysis of the hydrogen peroxide.

According to the present invention, heat for the gasification is principally supplied from the evaporation surface and is transported by an amount of transport air minimized for transportation, thus succeeding in preventing dilution of the mixture gas and suppressing pyrolysis of the hydrogen peroxide due to high temperatures to thereby eliminate the above problems encountered in the known method and apparatus.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. A method of sterilizing an object to be sterilized, said method comprising:

dropping hydrogen peroxide in the form of liquid droplets having a diameter of 1 to 3 mm. onto an evaporation surface of a heater, whereby said hydrogen peroxide liquid is instantaneously gasified, said heater being heated to a temperature between 140 and 180 degrees C., whereby decomposition of hydrogen peroxide during said gasification is minimized;

sweeping said hydrogen peroxide gas from the evaporator surface by transport air heated to a temperature which is at least substantially equal to the temperature of said evaporation surface to a surface of an object to be sterilized through a guide pipe heated to a temperature which is at least substantially equal to the temperature of said evaporation surface;

condensing said hydrogen peroxide gas at about ambient pressure at said surface of said object, said surface of said object being maintained at a temperature which is lower than the condensing temperature of said hydrogen peroxide gas so as to sterilize said object; and removing condensed hydrogen peroxide from said object by drying with hot air.

2. A sterilization apparatus comprising:

(1) means for forming droplets of liquid hydrogen peroxide fluidly connected to a source of liquid hydrogen peroxide wherein the diameters of said liquid droplets are between 1 and 3 mm., said liquid hydrogen peroxide being fed to the forming means by a constant amount feeder means;

(2) an evaporator surface disposed such that said formed droplets are dropped thereunto;

(3) a heater means associated with the evaporator surface such that said evaporator surface is maintained at a temperature between 140 and 180 degrees C. while said liquid droplets are dropped thereonto, whereby the liquid droplets are instantaneously gasified to hydrogen peroxide gas and the decomposition of the hydrogen peroxide during said gasification is minimized;

(4) transport air supply means for supplying transport air near said evaporator surface for transporting the gasified hydrogen peroxide to articles to be sterilized;

(5) guide means for guiding said gasified hydrogen peroxide contained in said transport air to objects to be sterilized, said guide means having heating means for maintaining the temperature of the gasified hydrogen peroxide and transport air at least at the evaporation temperature of the hydrogen peroxide.

3. A sterilization apparatus according to claim 2, wherein said forming means comprises nozzles open to a gasifying chamber, and a constant amount supply pump connected to said nozzles.

4. A sterilization apparatus according to claim 3, wherein said transport air supply means comprises an air supply pipe having a portion, internal of said chamber, which is formed with air supply holes open to said chamber and an internal extension in which a heater is inserted

* * * * *